United States Patent [19]

Hashizume et al.

[11] 4,286,101

[45] Aug. 25, 1981

[54] PROCESS FOR PREPARING TEREPHTHALIC ACID

[75] Inventors: Hiroshi Hashizume, Kitakyushi; Sigeki Harada, Nakama, both of Japan

[73] Assignee: Mitsubishi Chemical Industries Ltd., Fujuoka, Japan

[21] Appl. No.: 84,153

[22] Filed: Oct. 12, 1979

[30] Foreign Application Priority Data

Oct. 19, 1978 [JP] Japan ................................ 53-128709

[51] Int. Cl.$^3$ ............................................. C07C 51/42
[52] U.S. Cl. .................................................... 562/487
[58] Field of Search ........................................ 562/487

[56] References Cited

U.S. PATENT DOCUMENTS 3,859,344   1/1975   Shigeyasu et al. .................... 562/487

FOREIGN PATENT DOCUMENTS 46-11170   3/1971   Japan ...................................... 562/487

Primary Examiner—Alan Siegel
Attorney, Agent, or Firm—Oblon, Fisher, Spivak, McClelland & Maier

[57] ABSTRACT

Preparation of terephthalic acid by oxidizing p-xylene with molecular oxygen in an acetic acid solvent in the presence of a catalyst containing at least one heavy metal and bromine. Preparation of terephthalic acid of high purity accompanied by low level of combustion of the acetic acid solvent can be achieved by (i) introducing p-xylene and molecular oxygen into a first reaction zone kept at a temperature of 180°–230° C. to oxidize at least 95% by weight of the p-xylene into terephthalic acid;

(ii) introducing the reaction mixture obtained from the first reaction zone into a second reaction zone kept at a temperature of 0°–50° C. below the temperature of the first reaction zone in which the reaction mixture is subjected to post-oxidation with molecular oxygen without supplying p-xylene; and (iii) introducing the reaction mixture obtained from the second reaction zone into a third reaction zone kept at a temperature of at least 230° C. in which the reaction mixture is subjected again to post-oxidation with molecular oxygen without supplying p-xylene, and subjecting the resulting reaction mixture to crystallization and then to solid-liquid separation to recover terephthalic acid.

7 Claims, No Drawings

PROCESS FOR PREPARING TEREPHTHALIC ACID

BACKGROUND OF THE INVENTION

1. Field of the Invention

This invention relates to a process for preparing terephthalic acid of high purity, more particularly it relates to a process for preparing terephthalic acid of such high purity that permits it to be reacted directly with a glycol for the production of a polyester.

2. Description of the Prior Art

Terephthalic acid is useful as a starting material for polyesters and has usually been prepared by the so-called SD method wherein p-xylene is oxidized with molecular oxygen in an acetic acid solvent in the presence of a heavy metal-containing catalyst. However, the terephthalic acid product obtained by the SD method usually contains a relatively large amount (on the order of 1,000 to 3,000 ppm) of by-product 4-carboxybenzaldehyde (hereinafter referred to as 4CBA") and therefore it cannot be used as a starting material for the production of polyesters for use as fibers, films and the like as it is.

As a result, in the prior art technique the terephthalic acid is reacted with methanol to convert it into dimethyl terephthalate, which is then purified and reacted with a glycol. Alternatively, in recent years, there have developed processes for the purification of the crude terephthalic acid produced by the SD method which comprise dissolving it at an elevated temperature and pressure and contacting the resulting solution with a noble metal catalyst such as palladium, thereby providing a highly pure terephthalic acid containing not more than 30 ppm of 4CBA. However, the former purification technique is disadvantageous in that methanol is inevitably formed during the process of polyester production because of the use of dimethyl terephthalate as one of the starting materials for polyesters. While preferred in that the terephthalic acid can be purified as such, the latter technique requires two separate plant systems because there are differences in the solvents, catalysts and operating conditions employed between the preparation and purification processes of terephthalic acid.

More recently, an attempt has been made to prepare a highly pure terephthalic acid directly in a single plant by employing a particular combination of catalyst, oxidation conditions and oxidation mode. For example, a so-called post-oxidation technique has been known as a means for improving the purity of the terephthalic acid products prepared in oxidation plants of p-xylene. According to this technique, the slurry of terephthalic acid discharged from the oxidation reactor in which p-xylene is oxidized is treated with molecular oxygen at a relatively high temperature before the desired terephthalic acid is recovered from the slurry by solid-liquid separation. The purpose of this treatment is the removal of any intermediate, coloring contaminant and other impurity. More specifically, there is disclosed treatment of the slurry of terephthalic acid with molecular oxygen at a temperature above the reaction temperature (Japanese Patent Publication No. 12695/65) or at a temperature below the reaction temperature (Japanese Patent Laid-open (KOKAI) Nos. 16630/76, 39642/76, 85136/77 and 37636/78). Another unique technique in which the post-oxidation is carried out intermittently in a batchwise operation has also been disclosed (Japanese Patent Laid-open No. 31947/72).

Among these techniques, the post-oxidation effected at a temperature below the reaction temperature produces the most favorable results and affords the desired product of relatively high purity as compared with the terephthalic acid products obtained by the conventional process comprising only a single-step oxidation of p-xylene. However, the terephthalic acid products obtained by such lower temperature post-oxidation technique still contain 100 to 500 ppm of 4CBA, which is the limit of 4CBA level attained in commercial-scale operation of this technique. Although such terephthalic acid products can directly be used in polymerization with a glycol without further purification, but they are of medium purity and are inferior in purity to those products which have been subjected to the above-mentioned purification treatment with palladium or other catalyst.

Therefore, there is a continuing need for more economically attractive processes for the preparation of terephthalic acid of high purity in a single plant.

SUMMARY OF THE INVENTION

The present invention resides in a process for preparing terephthalic acid of high purity by oxidizing p-xylene with molecular oxygen in an acetic acid solvent in the presence of a catalyst containing at least one heavy metal and bromine, characterized by (i) introducing p-xylene and molecular oxygen into a first reaction zone kept at a temperature of 180°–230° C. to oxidize at least 95% by weight of the p-xylene into terephthalic acid;

(ii) introducing the reaction mixture obtained from the first reaction zone into a second reaction zone kept at a temperature 0°–50° C. below the temperature of the first reaction zone in which the reaction mixture is subjected to post-oxidation with molecular oxygen without supplying p-xylene; and (iii) introducing the reaction mixture obtained from the second reaction zone into a third reaction zone kept at a temperature of at least 230° C. in which the reaction mixture is subjected again to post-oxidation with molecular oxygen without supplying p-xylene, and subjecting the resulting reaction mixture to crystallization and then to solid-liquid separation to recover terephthalic acid.

DETAILED DESCRIPTION OF THE PREFERRED EMBODIMENTS

This invention is directed to a process for preparing terephthalic acid in a single plant having such high purity that permits it to be reacted directly with a glycol for the production of a polyester.

Further details of the present invention will be found in the following description.

In the process of this invention, terephthalic acid is prepared by oxidizing p-xylene with molecular oxygen in an acetic acid solvent in the presence of a heavy metal-containing catalyst.

In accordance with this invention, p-xylene is introduced into a first reaction zone in which at least 95%, preferably at least 98% by weight of the p-xylene is oxidized into terephthalic acid at a temperature of 180° to 230° C., preferably 205° to 225° C. and a pressure of 1 to 100 kg/cm$^2$, preferably 10 to 40 kg/cm$^2$. A much lower reaction temperature does not oxidize p-xylene to a satisfactory extent, while a much higher temperature not only cannot afford terephthalic acid of high purity, but cause an increase in combustion loss of the acetic acid solvent.

The reaction time in the first reaction zone should be sufficient to oxidize at least 95% by weight of the p-xylene feed into terephthalic acid, and it is generally 30 to 200 minutes and preferably 40 to 150 minutes.

The catalyst used in the process of this invention usually comprises a cobalt-manganese-bromine ternary system. For example, a useful catalyst comprises a cobalt compound in an amount of 120 to 600 ppm, preferably 200 to 400 ppm as cobalt metal based on the weight of the solvent, a manganese compound sufficient to provide a manganese/cobalt weight ratio of 0.5 to 1.5, and a bromine compound in an amount of 500 to 2,000 ppm, preferably 600 to 1,500 ppm as bromine based on the weight of the solvent. Typical of these compounds are such cobalt compounds as cobalt acetate and cobalt naphthenate, such manganese compounds as manganese acetate and manganese naphthenate and such bromine compounds as hydrogen bromide, sodium bromide, cobalt bromide and manganese bromide. Of course, manganese bromide and cobalt bromide can serve as a source of two catalytic components.

The weight ratio of the solvent to p-xylene fed to the first reaction zone is usually 2:1 to 5:1. If this ratio is much lower, the contents of the reactor cannot be stirred thoroughly. Such a smaller proportion of the solvent is also undesirable in that the second-stage post-oxidation procedure as described below cannot be performed satisfactorily during the third step. The acetic acid solvent may contain, for example, up to 20% by weight of water. The molecular oxygen passed through the liquid phase in the first reaction zone is usually in the form of air and is fed in an amount of 3 to 100 moles per mole of p-xylene.

In the first reaction zone, the water content of the liquid phase within the oxidation reaction may be controlled, for example, at a level of 5 to 15% by weight by cooling the condensable gas from the reactor and removing a part of the resulting condensate out of the reaction system without recycling it into the reactor.

Also 4CBA concentration in the mother liquor of the reaction mixture within the oxidation reactor may be controlled, for example, at a level of up to 2,000 ppm, preferably up to 1,500 ppm through adjustment of the reaction temperature, pressure, reaction time and catalytic system used in the first reaction zone. The control of the water content and 4CBA concentration in the oxidation reactor is desirable, since it gives satisfactory results in the subsequent second and third steps, yielding a final terephthalic acid product of outstandingly high purity.

The terephthalic acid-containing slurry produced in the first reaction zone is discharged therefrom and passed into a stirred tank reactor in a second reaction zone, in which the slurry is subjected to post-oxidation at a temperature of 0° to 50° C., preferably 2° to 30° C. below the reaction temperature in the first reaction zone without supplying p-xylene. If the post-oxidation is carried out at much lower temperature, it is impossible to sufficiently oxidize the oxidation intermediates present in the slurry. On the other hand, a higher temperature than that of the first reaction zone is not desirable, since it causes the formation of those impurities capable of acting as colored contaminants in a final terephthalic acid product. The post-oxidation procedure is usually continued for 20 to 90 minutes, preferably 30 to 60 minutes.

The vessel useful for the second reaction zone may be of the same type as the oxidation reactor used for the first reaction zone. Since the amount of the compounds to be oxidized in this post-oxidation step is very small, it is generally preferred in this step to use an inert gas-diluted air or the off-gas recovered from the first reaction zone as the source of the molecular oxygen. The amount of oxygen contained in such gas to be fed may be 1/10 to 1/1,000 the amount of oxygen to be fed to the first reaction zone.

In practice of the post-oxidation step, the oxidation can be achieved satisfactorily without adding further solvent and oxidation catalyst.

After the slurry has been subjected to post-oxidation in the second reaction zone, it is further subjected to post-oxidation once again (i.e., a second-stage post-oxidation) in the third reaction zone at a temperature of at least 230° C., preferably between 235° and 300° C. and most preferably between 240° and 260° C.

During the second-stage post-oxidation in the third reaction zone, at least a part of the terephthalic acid crystals which have been precipitated in the first and second reaction zones are dissolved in the solvent and subjected to the oxidation in solution. If the temperature in the third reaction zone is much lower, the terephthalic acid crystals cannot be dissolved sufficiently in the solvent and therefore the desired highly pure product cannot be obtained. On the other hand, a higher temperature is not desirable, since it is not economical due to the operational difficulty involved and it may possibly cause the formation of colored contaminants. The second-stage post-oxidation is generally continued for 5 to 120 minutes, preferably 20 to 60 minutes. As is the case of the second reaction zone, the molecular oxygen fed into the third reaction zone may be a diluted air or the oxidation off-gas and such a gas is fed in the proportion of 1/10 to 1/1,000 as oxygen to the amount of oxygen fed into the first reaction zone. If the amount of oxygen in the third reaction zone is insufficient, colored contaminants may possibly be formed. For this reason, it is desirable to prevent oxygen deficiency in the third reaction zone.

In accordance with the process of this invention, those oxidation intermediates present in the mother liquor of the slurry resulting from the first reaction zone are subjected to post-oxidation in the second reaction zone, whereas those oxidation intermediates included in the terephthalic acid crystals are subsequently oxidized in the third reaction zone via at least partial dissolution of the precipitated terephthalic acid crystals. Thus, the products obtained by the present process are of outstandingly high purity. If the slurry is directly subjected to the oxidation of the third step without being passed through the second reaction zone, the terephthalic acid product recovered are of inferior quality and contains appreciably larger amounts of colored contaminants.

The liquid reaction mixture from the third reaction zone is then subjected to crystallization in the conventional manner.

Preferably, the crystallization is performed stepwise by gradually decreasing both the temperature and pressure. Subsequently, a solid-liquid separation procedure such as centrifugal separation is conducted to recover the crystalline terephthalic acid. If necessary, the collected terephthalic acid crystals are washed with water, acetic acid or other suitable liquid and then dried to provide a final product. The mother liquor of the reaction mixture is usually passed to a distillation column in which the water and any other by-product formed and the catalyst are removed and acetic acid is recovered. Alternatively, since in accordance with the present process the mother liquor contains only minimum amounts of by-products, particularly those impurities interfering with the oxidation, 10 to 80% by weight of the mother liquor may be recycled directly into the oxidation reactor used as the first reaction zone.

From the foregoing detailed description, it will be apparent to those skilled in the art that the present process makes it possible to prepare in a single plant terephthalic acid of as high purity as the conventional purified products obtained by the purification treatment with palladium, for example, terephthalic acid having a 4CBA content of up to 50 ppm. Thus, the process of this invention is quite an economically attractive one for the preparation of highly pure terephthalic acid.

In addition, in accordance with the process for the oxidation of p-xylene comprising the three steps which are main oxidation and post-oxidations at lower and higher temperatures, terephthalic acid of medicum purity can also be prepared which has a 4CBA content of, for example, 100 to 500 ppm and which is capable of being reacted directly with a glycol. In this case, the amount of the acetic acid solvent lost by combustion throughout the oxidation is considerably smaller than that for the prior art process for the production of terephthalic acid of same purity comprising two steps which are main oxidation and post-oxidation at lower temperature.

The two-step post-oxidation of this invention makes it possible to finally obtain highly pure terephthalic acid, even though the quality of terephthalic acid obtained in the main oxidation step is lowered to a greater extent as compared with the prior art processes comprising the two-step oxidation. For example, in the process of this invention, when the other conditions are the same as those of the prior and processes, the shortening of the residence time in the main oxidation step can be accomplished to considerably lower the combustion loss of the acetic acid solvent.

Such a difference in combustion loss of the acetic acid solvent in a commercial process for large-scale production of terephthalic acid is of important significance from an economical viewpoint.

Having generally described this invention, a more complete understanding can be obtained by comparative examples and examples which are provided herein for purposes of illustration only and are not intended to be limiting in any manner.

EXAMPLE 1

A 10-liter titanium autoclave equipped with a reflux condenser at the top, an air supplying device at the bottom and an external heater and stirrer was charged with 3,000 g of hydrous acetic acid (of 5 wt. % water content) containing 4.44 g of cobalt acetate (as tetrahydrate), 4.68 g of manganese acetate (as tetrahydrate) and 6.70 g of hydrobromic acid (in aqueous 47% solution). While the reactor was kept at a temperature of 210° C. and a pressure of 25 kg/cm² gage, p-xylene was fed to the reactor at a rate of 1,300 g/hr. and simultaneously oxygen is passed through the reactor at a rate sufficient to maintain the oxygen content of the reactor off-gas at 4 to 5% by volume. Under these conditions the reaction was continued for 48 minutes.

Immediately after the reaction, the resulting slurry was transferred to a similar autoclave for use in the post-oxidation procedures, and subjected at first to post-oxidation with a diluted air at a temperature of 190° C. and a pressure of 18 kg/cm² gage for 30 minutes. Subsequently the slurry was heated and subjected again to post-oxidation (i.e., second-stage post-oxidation) with a diluted air at a temperature of 250° C. and a pressure of 37 kg/cm² gage for 30 minutes.

The solution thus obtained was cooled to precipitate terephthalic acid crystals, which were isolated and recovered by centrifugal separation. The 4CBA content and percent transmission of the collected terephthalic acid were determined after it was washed with acetic acid and dried. The results are shown in Table 1 below.

EXAMPLES 2–4

Following the procedures of Example 1, but using different temperatures in oxidation and the first-stage post-oxidation steps and different temperature, pressure and reaction time in the second-stage post-oxidation step as indicated in Table 1, a similar reaction was carried out and the terephthalic acid product was analyzed in the same way.

COMPARATIVE EXAMPLE 1

The procedures employed were the same as described in Example 1 except that the second-stage post-oxidation in the third step was omitted. The terephthalic acid product obtained after the second step was analyzed.

COMPARATIVE EXAMPLE 2

Following the general procedures of Example 1, the slurry obtained in the first step was directly heated without the post-oxidation in the second step and subjected to oxidation under the same conditions as the second-stage post-oxidation in the third step of Example 1. Analysis of the product was made in the same way.

COMPARATIVE EXAMPLE 3

Following the general procedures of Example 1, but using another temperature in the second-stage post-oxidation of the third step as indicated in Table 1, p-xylene was oxidized and analysis of the product was made in the same way.

TABLE 1

|  | 1st Step Temp. (°C.) | 2nd Step Temp. (°C.) | 3rd Step Temp. (°C.) | 3rd Step Pressure (Kg/cm² gage) | 3rd Step Time (min.) | 4CBA Concentration in terephthalic acid (ppm) | *% Transmission (T340) |
|---|---|---|---|---|---|---|---|
| Example 1 | 210 | 190 | 250 | 37 | 30 | 35 | 91.0 |
| 2 | 210 | 190 | 240 | 33 | 90 | 48 | 90.5 |
| 3 | 220 | 200 | 250 | 37 | 30 | 20 | 91.5 |
| 4 | 220 | 200 | 240 | 33 | 90 | 43 | 91.2 |
| Comparartive Example 1 | 210 | 190 | — | — | — | 1,500 | 55 |
| 2 | 210 | — | 250 | 37 | 30 | 350 | 81 |

TABLE 1-continued

| | 1st Step Temp. (°C.) | 2nd Step Temp. (°C.) | 3rd Step | | | 4CBA Concentration in terephthalic acid (ppm) | *% Transmission (T340) |
| --- | --- | --- | --- | --- | --- | --- | --- |
| | | | Temp. (°C.) | Pressure (Kg/cm² gage) | Time (min.) | | |
| 3 | 210 | 190 | 220 | 30 | 90 | 320 | 82 |

*The percent transmission (T340) was determined as a solution of 7.5 g of terephthalic acid in 50 cc of aqueous 2N potassium hydroxide at 340 nm using a spectrophotometer having a cell of 1 cm in light pass length.

EXAMPLE 5

Following the procedures of Example 1, but using different residence times in the first to third steps as indicated in Table 2 below, terephthalic acid of medium purity was prepared.

The 4CBA content, percent transmission of the collected terephthalic acid and the amount of acetic acid lost by combustion during the reaction were determined. The results are shown in Table 2 below.

COMPARATIVE EXAMPLE 4

Following the procedures of Comparative Example 1, but using different residence times in the first to third steps as indicated in Table 2 below, terephthalic acid of approximately the same quality as that of the terephthalic acid obtained in Example 5 was produced. Analysis of the product was made in the same way as that of Example 5. The results are shown in Table 2 below.

TABLE 2

| | Residence time (min.) | | | 4CBA Concentration in terephthalic acid (ppm) | % Transmission (T340) | *Relative amount of acetic acid combusted (Ex. 5 = 100) |
| --- | --- | --- | --- | --- | --- | --- |
| | 1st Step | 2nd Step | 3rd Step | | | |
| Example 5 | 30 | 30 | 30 | 220 | 89 | 100 |
| Comparative Example 4 | 120 | 30 | — | 200 | 91 | 260 |

*The relative amount of acetic acid combusted was determined by measuring the concentrations of CO and CO₂ in the reactor off-gas, calculating the amount of acetic acid combusted on the basis of the concentrations of CO and $CO_2$ and comparing the thus obtained value with that of Example 5 which was arbitrarily designated as 100.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. In a process for preparing terephthalic acid of high purity by reacting p-xylene with molecular oxygen in an acetic acid solvent in the presence of a catalyst containing at least one heavy metal and bromine, the improvement comprising the steps of:

(i) introducing p-xylene and molecular oxygen into a first reaction zone kept at a temperature of 180°–230° C. to oxidize at least 95% by weight of the p-xylene into terephthalic acid thereby forming a terephthalic acid—containing slurry;

(ii) introducing the terephthalic acid—containing slurry from the first reaction zone into a second reaction zone kept at a temperature 2°–30° C. below the temperature of the first reaction zone in which the terephthalic acid—containing slurry is subjected to post-oxidation with molecular oxygen without supplying p-xylene, whereby oxidation intermediates present in the mother liquor of the slurry are oxidized; and, (iii) introducing the terephthalic acid—containing slurry from the second reaction zone into a third reaction zone kept at a temperature of at least 230° C. in which the terephthalic acid—containing slurry is subjected again to post-oxidation with molecular oxygen without supplying p-xylene, whereby at least a part of the terephthalic acid crystals in the slurry are dissolved and those oxidation intermediates occluded in the terephthalic acid crystals are oxidized, and subjecting the resulting reaction mixture to crystallization and then to solid-liquid separation to recover terephthalic acid.

2. The process according to claim 1, wherein the post-oxidation in the second reaction zone is continued for 20 to 90 minutes.

3. The process according to claim 1, wherein the amount of oxygen to be fed to the second reaction zone for post-oxidation is 1/10 to 1/1,000 the amount of oxygen to be fed to the first reaction zone.

4. The process according to claim 1, wherein the post-oxidation in the third reaction zone is continued for 5 to 120 minutes.

5. The process according to claim 1 wherein the amount of oxygen to be fed to the third reaction zone for post-oxidation is 1/10 to 1/1,000 the amount of oxygen to be fed to the first reaction zone.

6. The process according to claim 1 wherein the temperature of the third reaction zone for post-oxidation is 235° to 300° C.

7. The process according to claim 1, wherein at least a part of the mother liquor separated from the desired product by the solid-liquid separation is recycled into the first reaction zone.

* * * * *